United States Patent [19]

Honoshofsky

[11] Patent Number: 5,078,602

[45] Date of Patent: Jan. 7, 1992

[54] SALIVA EJECTOR AND METHOD FOR CLEANING THE SAME

[76] Inventor: Geraldine Honoshofsky, 131 S. Mill St., Wellington, Ohio 44090

[21] Appl. No.: 516,985

[22] Filed: Apr. 30, 1990

[51] Int. Cl.$^5$ .................. A61C 17/06; A61C 17/14
[52] U.S. Cl. ............................. 433/91; 433/93
[58] Field of Search ............... 433/93, 94, 96, 91

[56] References Cited

U.S. PATENT DOCUMENTS

| | | | |
|---|---|---|---|
| 1,053,965 | 2/1913 | Barghausen et al. | 433/93 |
| 1,742,080 | 12/1929 | Jones | 433/93 X |
| 2,603,870 | 7/1952 | Nordin | 32/33 |
| 2,830,371 | 4/1958 | Dahl | 32/33 |
| 3,631,598 | 1/1972 | Lussier | 32/33 |
| 3,777,756 | 12/1973 | Lohr | 128/276 |
| 3,802,081 | 4/1974 | Rogers | 32/33 |
| 4,017,975 | 4/1977 | Johnson | 32/33 |
| 4,215,984 | 8/1980 | Reichley | 433/93 |
| 4,325,695 | 4/1982 | Sundelin et al. | 433/91 |
| 4,781,587 | 11/1988 | Kubo | 433/93 |

FOREIGN PATENT DOCUMENTS

| | | | |
|---|---|---|---|
| 120653 | 7/1930 | Austria | 433/94 |
| 595079 | 3/1960 | Canada | 433/91 |
| 1045161 | 11/1905 | France | 433/94 |
| 822045 | 4/1930 | France | 433/93 |
| 2595939 | 9/1987 | France | 433/91 |
| 232234 | 5/1944 | Sweden | 433/93 |
| 12072 | of 1915 | United Kingdom | 433/93 |
| 778544 | 7/1957 | United Kingdom | 433/93 |

Primary Examiner—Robert P. Swiatek
Assistant Examiner—Nicholas D. Lucchesi
Attorney, Agent, or Firm—Shlesinger, Arkwright & Garvey

[57] ABSTRACT

A saliva ejector including a hollow tube operably associated with a tongue protector. The tube includes first and second ends and a hollow cavity extending therebetween. The tongue protector is permanently secured to the tube by a solder having a minimum composition of 55% silver. The tongue protector is removed from the hollow cavity of the tube. The first end of the tube is adapted to be inserted into a patient's mouth and the second end is adapted to be operably associated with a vacuum system. The tube includes at least one aperture extending transversely therethrough and communicating with the hollow cavity thereby defining a passageway for saliva and the like to pass through. The tube has substantially constant inner and outer diameters.

21 Claims, 2 Drawing Sheets

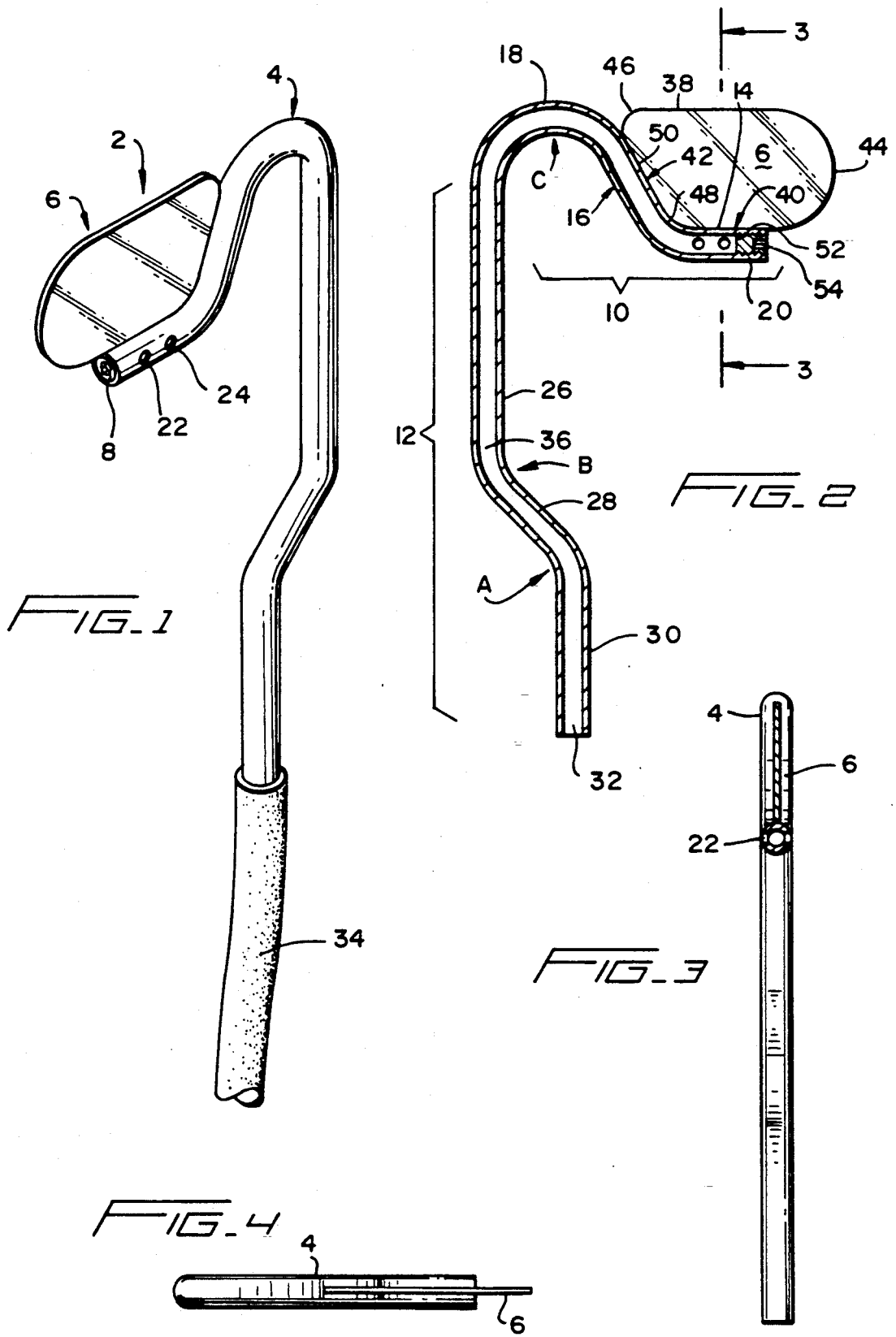

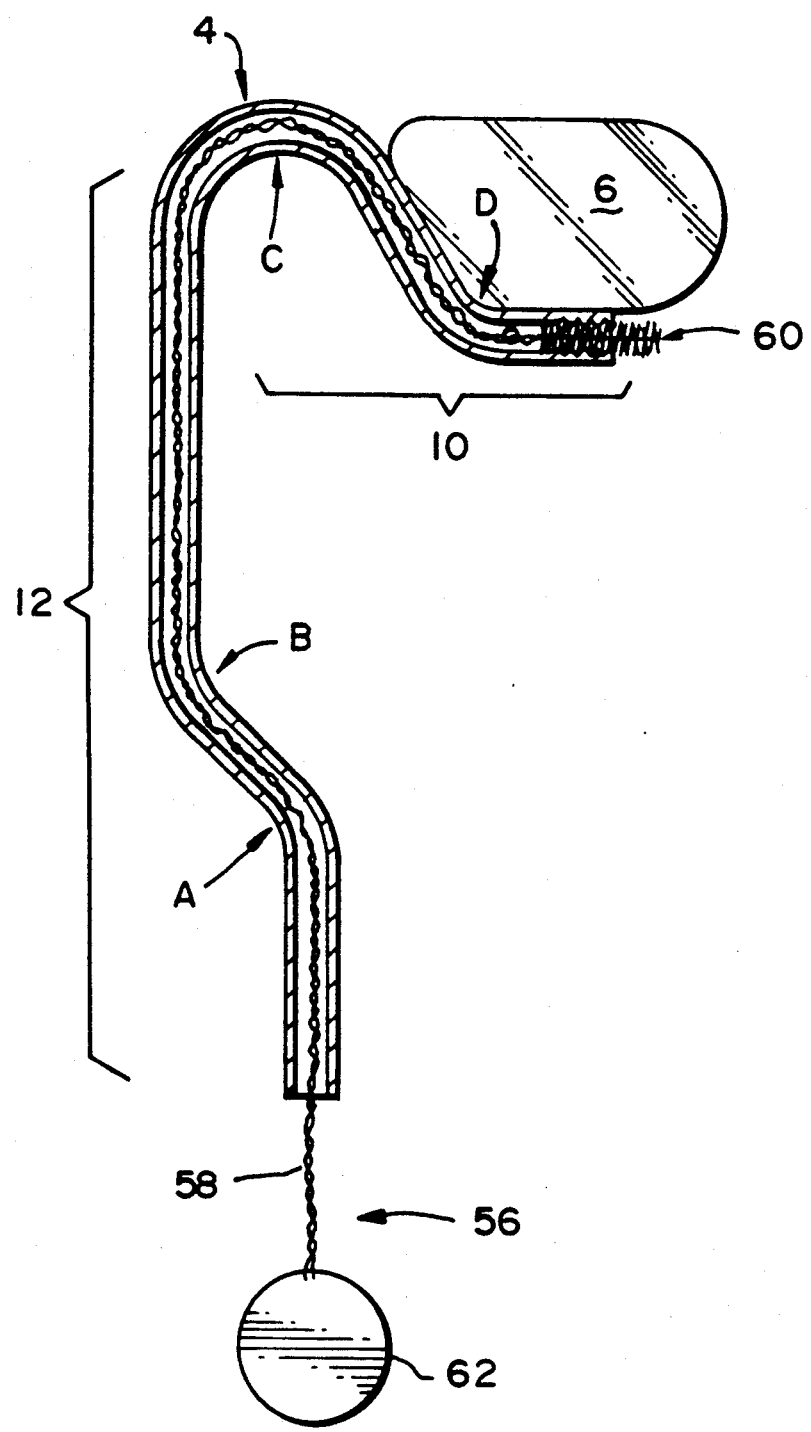

SALIVA EJECTOR AND METHOD FOR CLEANING THE SAME

FIELD OF THE INVENTION

The present invention relates to a saliva ejector for aspirating saliva from a patient's mouth and a method for cleaning the same. More specifically, the invention pertains to saliva ejectors including a tongue protector for protecting the patient's tongue from injury by dental instruments and the like.

BACKGROUND OF THE INVENTION

Saliva ejectors are widely used by both dentists and hygienists to aspirate saliva and the like from a patient's mouth while they are attending to the patient's teeth. Previously known saliva ejectors generally include a hollow tubular element connected at one end to a tongue protector and at the opposite end to a vacuum suction system. The tongue protector prevents injury to the patient's tongue by sharp dental instruments and the like. Openings are formed in either the tongue protector or the hollow tubular element. These openings in conjunction with the hollow tubular element and the vacuum suction system maintain the patient's mouth in a semi-dry state. Various conventional saliva ejectors are illustrated in U.S. Pat. Nos. 2,603,870; 2,830,371; 3,631,598; 3,777,756; 3,802,081; 4,017,975; and 4,325,695.

The above identified conventional saliva ejectors have several inherent disadvantages associated therewith. Specifically, conventional saliva ejectors consist of a plurality of components which must be disassembled prior to cleaning thereof and reassembled for use. Further, the individual components include a plurality of hard to reach recesses, notches and the like where bacteria, blood spores and similar debris can become lodged thus making it more difficult to clean the same. Moreover, the openings formed in known saliva ejectors for receiving saliva are partially or wholly obstructed by one or more of the components. Furthermore, hollow tubular elements include sections forming severely acute angles making it difficult or impossible to insert a percolator type brush through the tubular element to clean the same.

OBJECTS AND SUMMARY OF THE INVENTION

An object of the present invention is to provide an improved saliva ejector overcoming the aforementioned disadvantages of conventional saliva ejectors.

Another object of the present invention is to provide a saliva ejector that can be cleaned without detaching the tongue protector therefrom.

Yet a further object of the present invention is to provide a tubular element, one end of which is operably associated with a patient's mouth and the other end of which is connected to with a vacuum suction system, with an inner surface free from recesses, notches, stepped portions and the like.

Still another object of the present invention is to provide the tubular element with an outer surface free from recesses, notches, stepped portions and the like.

A further object of the present invention is to provide a saliva ejector having a tongue protector secured to a hollow tubular element removed from the hollow cavity extending therethrough.

Yet another object of the present invention is to provide openings for receiving saliva in the tubular element free from any obstructions.

Another object of the present invention is to reduce the severity of the angled sections formed in a saliva ejector.

Still a further object of the present invention is to provide a saliva ejector adapted to maintain the suction tube of the vacuum suction system against the patient's body thereby reducing the likelihood of saliva ejector from being disconnected from the vacuum suction system.

Further objects and advantages of the present invention will be readily understood from the following detailed description of the invention.

In summary, the preferred embodiment of the present invention is directed to a saliva ejector having a tubular element and a tongue protector operably associated therewith. The tubular element includes first and second spaced open ends and a hollow cavity extending therebetween. A plug is inserted in the first end and the second end is connected to a vacuum suction system. A pair of openings extend through the sidewalls of the tubular element adjacent the first end and communicate with the hollow cavity. The tongue protector is permanently secured to the outer surface of the tubular element adjacent the first end and removed from the hollow cavity.

DETAILED DESCRIPTION OF THE DRAWINGS

FIG. 1 is a perspective view of a saliva ejector formed in accordance with the preferred embodiment of the present invention.

FIG. 2 is a cross-sectional side elevational view of the preferred embodiment of the present invention.

FIG. 3 is a cross-sectional front elevational view of the preferred embodiment of the present invention taken along lines 3—3 in FIG. 2.

FIG. 4 is a plan view of the preferred embodiment of the present invention.

FIG. 5 is a cross-sectional side elevational view depicting a percolator type brush inserted into the preferred embodiment of the present invention.

DETAILED DESCRIPTION OF THE DRAWINGS

The preferred embodiment of the present invention will hereinafter be described.

FIGS. 1 through 4

Referring to FIGS. 1 and 2, a saliva ejector 2 includes a hollow tubular element 4, a plate 6, and a threaded plug 8. The hollow tubular element 4 includes a first section 10 and a second section 12. The first section 10 includes a first end portion 14, an inclined intermediate portion 16 and an arcuate second end portion 18. The first end portion 14 includes a threaded opening 20 formed therein. In the preferred embodiment, the intermediate portion 16 forms an angle of 27° with a vertical axis when the end portion 14 is oriented at a 90° angle thereto. Apertures 22 and 24 extend through the first end portion 14 and are removed from threaded opening 20.

Second section 12 includes a first longitudinally extending portion 26, an inclined portion 28 and a second longitudinally extending portion 30. In the preferred embodiment, the center line of the first portion 26 is offset .68 inches from the center line of the second portion 30 and inclined portion 28 forms a 45 angle with the vertical axis. First portion 26 extends substantially parallel to second portion 30. Second portion 30 includes an open end 32 formed therein. The open end 32 of tubular element 4 is secured to a flexible suction tube 34. The opposite end of suction tube 34 is connected to a conventional vacuum suction system (not shown). By offsetting portions 26 and 30, the suction tube 34 is maintained against the patient's body and out of the way of the attending dentist or hygienist.

The tubular element 4 includes a hollow cavity 36 extending between openings 20 and 32. The hollow cavity 36 communicates with apertures 22 and 24 thereby forming a passageway for aspirating saliva from a patient's mouth. Arcuate sections A, B, C, and D are formed over the length of tubular element 4 and have substantially the same radius of curvature. In the preferred embodiment, the radius of curvature for arcuate sections A, B, C, and D is 9/16 of an inch. The tubular element 4 has substantially constant inner and outer diameters along its length i.e. its outer and inner surfaces are substantially free from recesses, notches, stepped sections, and the like. In the preferred embodiment, the tubular element 4 has an outer diameter of 0.25 inches and a wall thickness of 0.035 inches.

Referring to FIG. 2, plate 6 includes an upper surface 38, a lower surface 40, left end 42, and right end 44. Upper surface 38 extends substantially parallel to lower surface 40 and first end portion 14. The left end 42 includes first and second spaced arcuate portions 46 and 48, respectively, and an inclined section 50. In the preferred embodiment, the inclined section 50 forms a 27° angle with the vertical axis. The inclined section 50, the arcuate section 48, and the lower surface 40 of plate 6 are permanently secured to the outer surface of tubular element 4. In the preferred embodiment, a solder with a minimum of 55% silver is used to secure plate 6 to element 4. It will be readily appreciated by one of ordinary skill in the art that plate 6 and tubular element 4 can be formed from one piece. The right end 44 of plate 6 extends beyond the opening 20 formed in tubular element 4. The plate 6 having a preferred thickness of 0.035 inches is removed from the hollow cavity 36 and apertures 22 and 24 of tubular element 4. Further, end 52 of plug 8 is removed from apertures 22 and 24. Thus, apertures 22 and 24 are unobstructed by any of the components of the saliva ejector 2. An aperture 54 is formed in end 52 to permit removal of plug 8 from threaded opening 20.

Preferably, tubular element 4, plate 6 and plug 8 are formed from stainless steel to prevent corrosion thereof and provide plate 6 with a mirrored surface.

METHOD OF CLEANING THE SALIVA EJECTOR OF THE PRESENT INVENTION

FIG. 5

The saliva ejector of the present invention is designed to be reused by dentists and hygienists. Accordingly, it is of the utmost importance that, it be free from bacteria, blood spores and similar debris prior to reuse. Thus, it is necessary that the saliva ejector be adapted to be readily and thoroughly cleaned. The method of cleaning the saliva ejector of the present invention will now be described.

An allen wrench (not shown) is inserted into aperture 54 to remove the plug 8 from threaded engagement with the opening 20 of tubular element 4. A percolator type brush 56 is inserted in either openings 20 or 32 to clean the hollow cavity 36 and is extended through the other of the openings 20 and 32 as seen in FIG. 5. The percolator type brush 56 has a length greater than the tubular element 4 and includes two intertwined wires 58, bristles 60 and a handle 62. This procedure can be repeated several times to insure that the hollow cavity 36 is thoroughly cleaned.

A number of previously known saliva ejectors have included acutely angled sections. In such saliva ejectors, it has not been possible to readily insert a percolator type brush through these sections. The tubular element 4 of the present invention has been designed to minimize the severity of its angled sections. Accordingly, percolator type brushes may be readily inserted through the length of the tubular element 4. Specifically, portion 28 is positioned at an angle of 45 degrees with respect to the vertical axis. Therefore, a percolator type brush traversing section 12 of the tubular element will undergo a directional change of only 45 degrees through each of the arcuate sections A and B. Further, first end portion 14 and inclined intermediate portion 16 form an obtuse angle thereby reducing the directional change of the percolator brush passing through section 10 of tubular element 4. In the preferred embodiment, arcuate sections A, B, C, and D have a radius of curvature of 9/16 of an inch measured from the center of the tubular element 4 to further ease the movement of the brush therethrough. The smooth inner and outer surfaces of tubular element 4 further expedite the cleaning of the saliva ejector 2.

Once the hollow cavity 36 is thoroughly cleaned, the plug 8 and the saliva ejector 2 are submersed in a well known cleaning solution and thereafter sterilized in the conventional manner.

It is readily apparent from the above discussion that the saliva ejector formed in accordance with the present invention is a significant improvement over previously known devices. Specifically, the ejector can be cleaned with minimal disassembly thereof. Further, a percolator type brush can be readily inserted through the hollow cavity of the saliva ejector without removing the tongue protector therefrom. Moreover, the tubular element is free from hard to reach recesses, notches, stepped portions, and the like where debris can permanently lodge.

While this invention has been described as having a preferred design, it is understood that it is capable of further modifications, uses and/or adaptations of the invention, following in general the principle of the invention, and including such departures from the present disclosure as come within known or customary practice in the art to which the invention pertains, and as may be applied to the central features hereinbefore set forth, and fall within the scope of the invention of the limits of the appended claims.

What I claim is:

1. A combined saliva ejector and tongue protector, comprising:
   (a) a tube means for permitting fluid to pass therethrough, said tube means having first and second ends and a hollow cavity, said first end is adapted to be inserted into a patient's mouth and said second end including means for receiving a vacuum suction system;

(b) plug means removably secured to said first end, said plug means including thread means for securing said plug means to said first end;

(c) a planar tongue protecting plate means for protecting a patient's tongue operably associated with said tube means adjacent said first end, said tongue protecting plate means including upper and lower surfaces, one of said upper and lower surfaces being permanently fixed to said tube means and the other of said upper and lower surfaces being removed from said tube means; and, (d) said tube means having a configuration which readily permits a brush means to be inserted into one of said first and second ends to pass through said tube means and out the other of said first and second ends.

2. An apparatus as in claim 1, wherein:
(a) said tube means has a substantially constant inner diameter.

3. An apparatus as in claim 2, wherein:
(a) said tube means has a substantially constant outer diameter.

4. An apparatus as in claim 1, wherein:
(a) said lower surface of said tongue protecting plate means is secured to said tube means removed from said hollow cavity.

5. An apparatus as in claim 1, wherein:
(a) said first end of said tube means includes a threaded opening formed therein; and
(b) said plug means includes a threaded plug adapted to be inserted into said threaded opening.

6. An apparatus as in claim 5, wherein:
(a) said threaded plug, said tube means and said tongue protecting plate means are formed from stainless steel.

7. An apparatus as in claim 1, wherein:
(a) said second end includes first and second sections, said first section is offset from said second section and extends substantially parallel thereto.

8. An apparatus as in claim 1, wherein:
(a) said tongue protecting plate means is permanently fixed to said tube means by a solder having a minimum composition of 55% silver.

9. A combined saliva ejector and tongue protector, comprising:
(a) a tube means for permitting fluid to pass therethrough, said tube means having an outer surface, an inner surface, a first end adapted to be inserted into a patient's mouth, a second end and a hollow cavity, said first end having an opening, said second end including means for receiving a vacuum suction system;
(b) a planar tongue protecting means for protecting a patient's tongue operably associated with said tube means adjacent said first end and being positioned removed from said hollow cavity of said tube means, said tongue protecting means having a lower surface and an upper surface, one of said lower surface and said upper surface being in abutting engagement with said outer surface of said tube means;
(c) said tube means having a configuration which readily permits a brush means to be inserted into one of said first and second ends to pass through said tube means and out the other of said first and second ends; and (d) plug means removably secured to said first end, said plug means including thread means for securing said plug means to said first end.

10. An apparatus as in claim 9, wherein:
(a) said tongue protecting means is permanently fixed to said tube means.

11. An apparatus as in claim 10, wherein:
(a) said tongue protecting means is removed from said opening of said first end.

12. An apparatus as in claim 9, wherein:
(a) said tube means has a substantially constant inner diameter.

13. An apparatus as in claim 12, wherein:
(a) said tube means has a substantially constant outer diameter.

14. An apparatus as in claim 9, wherein:
(a) said tongue protecting means includes a plate having a thickness less than an outer diameter of said tube means.

15. An apparatus as in claim 9, wherein:
(a) said tube means includes at least one aperture extending transversely therethrough and communicating with said hollow cavity, said at least one aperture is removed from said opening of said first end and said tongue protecting means.

16. An apparatus as in claim 9, wherein:
(a) said second end includes first and second sections, said first section is offset from said second section.

17. An apparatus as in claim 16, wherein:
(a) said first section extends substantially parallel to said second section.

18. An apparatus as in claim 17, wherein:
(a) said second section extends substantially perpendicular to at least a portion of said first end; and
(b) said perpendicular portion of said first end is adapted to be seated in the bottom of the patient's mouth.

19. An apparatus as in claim 17, wherein:
(a) said second end includes an intermediate section extending between said first and second sections, said intermediate section is inclined at an angle of 45° from a vertical axis.

20. A combined saliva ejector and tongue protector, comprising:
(a) tube means for permitting fluid to pass therethrough, said tube means having first and second ends and a hollow cavity, said first end is adapted to be inserted into a patient's mouth and said second end having means for receiving a vacuum suction system, said first end being disposed in substantially the same plane as said second end, said first end having an opening;
(b) a planar tongue protecting plate means for protecting a patient's tongue operably associated with said tube means adjacent said first end, said tongue protecting plate means including upper and lower surfaces, one of said upper and lower surfaces being permanently fixed to said tube means and the other of said upper and lower surfaces being removed from said tube means; and
(c) plug means removably secured to said first end, said plug means including thread means for securing said plug means to said first end.

21. A method for cleaning a combined saliva ejector and tongue protector, comprising the steps of:
(a) providing a tube means for permitting fluid to pass therethrough, the tube means having an outer surface, an inner surface, a first end, a second end and a hollow cavity, the first end having a plug means removably secured thereto, the first end being adapted to be inserted into a patient's mouth and the second end having means for receiving a vacuum suction system;

(b) providing a tongue protecting means for protecting a patient's tongue operably associated with the tube means adjacent the first end, the tongue protecting means having a lower surface and an upper surface, at least one of the lower and upper surfaces being secured to the outer surface of the tube means at the first end;

(c) removing the plug means from the first end of the tube means; and, (d) inserting a brush means into one of the first and second ends and extending the brush means through the other of the first and second ends while the tongue protecting means is secured to the first end of the tube means.

* * * * *